US007785846B2

(12) United States Patent
Boy et al.

(10) Patent No.: US 7,785,846 B2
(45) Date of Patent: Aug. 31, 2010

(54) METHOD FOR THE PRODUCTION OF METHIONINE

(75) Inventors: Matthias Boy, Langen (DE); Daniela Klein, Mannheim (DE); Hartwig Schröder, Nußloch (DE)

(73) Assignee: Evonik Degussa GmbH, Essen (DE)

( * ) Notice: Subject to any disclaimer, the term of this patent is extended or adjusted under 35 U.S.C. 154(b) by 30 days.

(21) Appl. No.: 10/583,304

(22) PCT Filed: Dec. 17, 2004

(86) PCT No.: PCT/EP2004/014423

§ 371 (c)(1),
(2), (4) Date: Jun. 15, 2006

(87) PCT Pub. No.: WO2005/059155

PCT Pub. Date: Jun. 30, 2005

(65) Prior Publication Data

US 2007/0122888 A1 May 31, 2007

(30) Foreign Application Priority Data

Dec. 18, 2003 (DE) ................................ 103 59 668

(51) Int. Cl.
*C12P 13/12* (2006.01)
(52) U.S. Cl. ...................................................... 435/113
(58) Field of Classification Search .................. None
See application file for complete search history.

(56) References Cited

U.S. PATENT DOCUMENTS

| 3,139,386 | A | * | 6/1964 | Takesue et al. | ............... 435/113 |
| 4,601,893 | A | | 7/1986 | Cardinal | |
| 5,053,328 | A | | 10/1991 | Muetze et al. | |
| 5,175,108 | A | | 12/1992 | Bachmann et al. | |
| 5,840,358 | A | | 11/1998 | Höfler et al. | |
| 6,017,555 | A | | 1/2000 | Stevens et al. | |
| 2002/0197605 | A1 | | 12/2002 | Nakagawa et al. | |
| 2005/0260721 | A1 | | 11/2005 | Kröger et al. | |
| 2006/0003425 | A1 | | 1/2006 | Kröger et al. | |
| 2006/0068476 | A1 | | 3/2006 | Kröger et al. | |
| 2006/0223149 | A1 | | 10/2006 | Kröger et al. | |

FOREIGN PATENT DOCUMENTS

| DE | 3533198 | 3/1987 |
| DE | 10136986 | 3/2002 |
| DE | 10217058 | 11/2003 |
| DE | 10222858 | 12/2003 |
| DE | 10239073 | 3/2004 |
| DE | 10239082 | 3/2004 |
| DE | 10239308 | 3/2004 |
| EP | 0472869 | 7/1991 |
| EP | 0809940 | 4/1997 |
| EP | 1108790 | 6/2001 |
| FR | 1331847 | 7/1963 |
| JP | 10229891 | 9/1998 |
| WO | WO-02/10209 | 2/2002 |
| WO | WO-03/087386 | 10/2003 |
| WO | WO-2005/007862 | 1/2005 |

OTHER PUBLICATIONS

Hsiao & Glatz, Biotechnology & Bioengineering, 1994, vol. 44, p. 1228-1234.*
Hermann, T., Journal of Biotechnology, Sep. 2003,vol. 104, p. 155-172.*
Kumar et al., Process Biochemistry, Mar. 2003, vol. 38, p. 1165-1171.*
Yuan et al., Journal of Chemical Technology and Biotechnology, 2002, vol. 77, p. 602-606.*
Kusumoto I., J. Nutr. 2001, vol. 131, p. 2552S-2555S.*
Hermann T., Journal of Biotechnology, Sep. 2003,vol. 104, p. 155-172.*
"Ionization Constants and pH Values at the Isoelectric Points of The Amino Acids in Water at 25°C." In Handbook of Chemistry and Physics, pp. C-741-C-743.
Hermann, T. "Industrial Production of Amino Acids by Coryneform Bacteria", Journal of Biotechnology, 2003, vol. 104, pp. 155-172.
Ullmann's Encyclopedia of Industrial Chemistry, 1985, vol. A2, pp. 71-72.
Motoyama, H., et al., "Overproduction of L-Lysine from Methanol by *Methylobacillus glycogenes* Derivatives Carrying a Plasmid with a Mutated dapA Gene", Applied and Environmental Microbiology, 2001, vol. 67, No. 7, pp. 3064-3070.
Eikmanns, B. J., et al., "Molecular Aspects of Lysine, Threonine, and Isoleucine Biosynthesis in Corynebacterium glutamicum", Antonie van Leeuwenhoek, 1993, vol. 64, pp. 145-163.
Eikmanns, B. J., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase", Journal of Bacteriology, 1992, vol. 174, No. 19, pp. 6076-6086.
Martin, J. F., et al., "Cloning Systems in Amino Acid-Producing Corynebacteria", Bio/Technology, 1987, vol. 5, pp. 137-146.
Guerrero, C., et al., "Directed Mutagenesis of a Regulatory Palindromic Sequence Upstream from the *Brevibacterium lactofermentum* Tryptophan Operon", Gene, 1994, vol. 138, pp. 35-41.
Tsuchiya, M., et al., "Genetic Control Systems of *Escherichia coli* Can Confer Inducible Expression of Cloned Genes in Coryneform Bacteria", Bio/Technology, 1988, vol. 6, pp. 428-430.
Eikmanns, B. J., et al., "A Family of *Corynebacterium glutamicum/Escherichia coli* Shuttle Vectors for Cloning, Controlled Gene Expression, and Promoter Probing", Gene, 1991, vol. 102, pp. 93-98.
Schwarzer, A., et al., "Manipulation of *Corynebacterium glutamicum* by Gene Disruption and Replacement", Bio/Technology, 1991, vol. 9, pp. 84-87.

(Continued)

*Primary Examiner*—L Blaine Lankford
*Assistant Examiner*—Kade Ariani
(74) *Attorney, Agent, or Firm*—Smith, Gambrell & Russell, LLP (57) ABSTRACT

The present invention relates to a process for producing methionine by fermentation, a process for isolating the methionine formed, the methionine-containing biomass produced in isolation, use thereof for producing a feedstuff or feed supplement, and also to the use of the isolated methionine for producing foodstuffs or feedstuffs or food supplements or feed supplements.

16 Claims, 4 Drawing Sheets

OTHER PUBLICATIONS

Reinscheid, D. J., et al., "Stable Expression of *hom-1-thrB* in *Corynbacterium glutamicum* and its Effect on the Carbon Flux to Threonine and Related Amino Acids", Applied and Environmental Microbiology, 1994, vol. 60, No. 1, pp. 126-132.

LaBarre, J., et al., "Gene Replacement, Integration, and Amplification at the *gdhA* Locus of *Corynebacterium glutamicum*", Journal of Bacteriology, 1993, vol. 175, No. 4, pp. 1001-1007.

Malumbres, M., et al., "Codon Preference in Corynebacteria", Gene, 1993, vol. 134, pp. 15-24.

Jensen. P. R., et al., "Artificial Promoters for Metabolic Optimization", Biotechnology and Bioengineering, 1998, vol. 58, Nos. 2 & 3, pp. 191-195.

Makrides, S.C., "Strategies for Achieving High-Level Expression of Genes in *Escherichia coli*" Microbiological Reviews, 1996, vol. 60, No. 3, pp. 512-538.

Pátek, M., et al., "Leucine Synthesis in *Corynebacterium glutamicum*: Enzyme Activities, Structure of *leuA*, and Effect of *leuA* Inactivation on Lysine Synthesis", Applied and Environmental Microbiology, 1994, vol. 60, No. 1, pp. 133-140.

Malakhova I. I., et al., "Thin-Layer Chromatography of Free Amino Acids. Selection of Conditions for the Separation of L-Lysine, L-Homoserine, and L-Threonine", Russian Biotechnology, 1996, No. 11, pp. 26-31.

Schmidt, S., et al., "Near Infrared Spectroscopy in Fermentation and Quality Control for Amino Acid Production", Bioprocess Engineering, 1998, vol. 19, pp. 67-70.

Roy, S. K., et al., "Production and Purification of Methionine from a Multi-Analog Resistant Mutant $B_6$US-215 of *Bacillus megaterium* B71", J. Microbial Biotechnology, 1989, vol. 4, No. 1, pp. 35-41.

\* cited by examiner

METHOD FOR THE PRODUCTION OF METHIONINE

RELATED APPLICATIONS

This application is a national stage application (under 35 U.S.C. 371) of PCT/EP2004/014423 filed Dec. 17, 2004, which claims benefit of German application 103 59 668.2 filed Dec. 18, 2003.

The present invention relates to a process for producing methionine by fermentation, a process for isolating the methionine formed, the methionine-containing biomass obtained in the isolation, its use for producing a feedstuff or feed supplement, and also to the use of the isolated methionine for producing foods or feeds or food or feed supplements.

PRIOR ART

Methionine is used in the most varied sectors, including the food, feed, cosmetics and pharmaceutical industries.

Hitherto, only the chemical production processes for D,L-methionine have been of industrial importance. Starting materials for this synthesis are hydrogen sulfide, methylmercaptan, acrolein, Prussic acid or methylmercaptopropionaldehyde (see Ullmann's Encyclopedia of Industrial Chemistry (1985), Vol. A2, page 71).

Methionine is also produced by natural cellular metabolic processes. Its production on an industrial scale would most expediently be carried out by means of bacterial cultures which have been developed to produce and secrete large amounts of the desired substance. Organisms which are particularly suitable for this purpose are nonpathogenic coryneform bacteria.

It is known that methionine can be produced by fermenting strains of coryneform bacteria in particular *Corynebacterium glutamicum*. Because of the great importance, work is continuously being carried out on improving the production process. Improvements on the process can relate to, for example, fermentation measures, the composition of the nutrient media, or the intrinsic performance properties of the microorganism itself.

To improve the performance properties of these microorganisms with respect to producing a defined molecule, use can be made of methods of mutagenesis, selection and mutant selection or methods of recombinant DNA technology for the strain improvement of amino acid-producing strains, for example of *Corynebacterium*, by amplifying or turning off individual amino acid biosynthesis genes and thus inducing an improvement of the amino acid production.

For instance, WO-A-02/10209 and DE-A-101 36 986 describe a process for producing L-methionine by fermentation, using L-methionine-producing genetically modified coryneform bacteria. There, a description is given, inter alia, of a process for producing L-methionine comprising the fermentation of the bacteria, the enrichment of the amino acid in the medium or in the bacteria and the isolation of the amino acid. Furthermore, a process is described for producing L-methionine-containing animal feed additive from a fermentation broth which comprises the following steps: a) fermenting L-methionine-producing microorganisms; b) concentrating the fermentation broth, for example by evaporation; c) separating off the biomass (0-100%), for example by centrifugation; and d) drying, for example by freeze drying or spray drying, spray granulation.

Swapan et al. describe, in J. Microbial Biotechnology, 4 (1), 35-41 (1989), the microbial production of methionine by means of a *Bacillus megaterium* mutant by separating off the cells from the fermentation broth, adjusting the pH to 5, treatment with activated carbon and ion-exchange chromatography.

DE-A-35 33 198 discloses the production of L-leucine by fermentation using special thermophilic bacteria. The fermentation is performed at +60° C. continuously with retention of biomass, separation of product-containing, spent medium, cooling (down to +2° C.) in a crystallizer, production of the amino acid which has crystallized out and recirculation of the mother liquor to the reactor. The production of methionine by fermentation is not described therein.

The processes which have been described hitherto for the microbial production of methionine do not yet satisfy the requirements of production on an industrial scale. A reason for this is, firstly, the limited solubility of methionine in the aqueous fermentation medium, which has the effect that, at high biosynthesis output, methionine precipitates out in the fermentation broth and thus makes purification difficult. A further reason is that in the case of work according to the prior art, considerable waste streams are produced, the disposal of which is associated with high cost.

BRIEF DESCRIPTION OF THE INVENTION

It is an object of the present invention, therefore, to provide an improved process for isolating methionine produced by fermentation which is applicable, in particular, to those fermentation broths which comprise methionine in part in crystalline form. A further object is to provide a workup process for methionine-containing fermentation broths which produces virtually no waste streams and thus can be carried out particularly economically.

We have found that the above object is surprisingly achieved by providing a workup process which specifically exploits the solubility properties of methionine for separating off the biomass. The process utilizes crystallization as a purification method for L-methionine produced by fermentation. It gives two different products for use as feed additive (low-concentration and high-concentration product). In preferred variants, virtually no waste streams are produced and thus particularly economical methionine production on an industrial scale is permitted.

DETAILED DESCRIPTION OF THE INVENTION

A) General Definitions

"Methionine", for the purposes of the invention, in principle covers L- or D-methionine, mixtures of these isomers, for example racemates, but preferably L-methionine.

The solubility of methionine in water is about 30 g/l at 20° C., and at 70° C. it is greater than 90 g/l. In the fermentation broth under these conditions, solubilities of comparable order of magnitude are observed.

Process measures such as "concentrating", "separating", "washing", "drying", for the purposes of the present invention, cover all processes present in the field of specialist skill. For example, "concentrating" can be taken to mean evaporating the liquid phase under atmospheric pressure or with the application of a vacuum. "Concentrating" can be carried out, for example, using familiar techniques, such as reverse osmosis or nanofiltration or customary apparatuses, for example a falling-film evaporator, thin-film evaporator or rotary evaporator, or combinations thereof. "Separating" can cover, for example, centrifuging, filtering, decanting, or combinations of these processes. "Washing" can cover, for example, filtering off a solid and single or repeated washing, if appropriate after suspending the filter residue. "Drying" can cover, for example, freeze drying, spray drying, spray granulation, fluidized-bed drying or combinations of these processes.

B) Preferred Embodiments of the Invention

The present invention firstly relates to a process for isolating methionine produced by fermentation, which comprises a) heating a methionine-containing liquid fraction produced in the fermentation of a methionine-producing microorganism, which liquid fraction comprises, in particular, methionine in partially undissolved form, to a temperature which is sufficient to increase the solubility of methionine in the liquid phase, preferably to bring methionine essentially completely into solution, b) obtaining therefrom a methionine-enriched liquid phase and c) crystallizing out methionine, if appropriate after concentrating the enriched liquid phase.

Methionine is "essentially" completely in solution if it is, for example, more than 95% dissolved, preferably more than 98% dissolved, in particular 100% dissolved, based on the total methionine content in the liquid phase.

A methionine-containing "liquid fraction" is typically the broth which is obtained from the fermentation process and comprises, in particular, methionine in partially undissolved form and if appropriate can have other solid constituents which can be customarily present in fermentation broths; or a liquid derived therefrom, obtained for example by suitable pretreatment. A "pretreatment" could consist, for example, in concentration by evaporation, or in addition of substances. For example, methionine-containing fractions could be added to the broth from previous workup batches, or adjuncts (see below) which promote the following processing steps or which promote the use of the product (for example a feed additive) as directed.

The content of undissolved methionine in the, if appropriate, fortified fermentation broth is, based on the total weight of the fermentation broth, in the range of from about 1 to 10% by weight, preferably from about 3 to 8% by weight, or, based on the total solids content, in the range of from about 30 to 80% by weight, preferably from about 50 to 57% by weight.

For example, an inventive fermentation can give a methionine content of about 96 g/l, of which, at a typical fermentation temperature, about 46 g/l are in solution and about 50 g/l are undissolved.

The methionine content of the enriched liquid phase is, based on the dry residues thereof, in the range of from about 60 to 100% by weight or about 90 to 100% by weight, as for example from about 75 to 85% by weight, or about 95 to 100% by weight, each based on dry mass.

To bring methionine essentially into solution, in stage a), the liquid is heated to a temperature in the range of from about 60 to 120° C., preferably from about 70 to 100° C., depending on the amount of the product to be dissolved. If appropriate, it can be necessary to operate under a slightly elevated pressure, for example from 1 to 5 atm.

Preferably, the liquid fraction used in stage a) is the biomass-containing fermentation broth without further pretreatment.

The methionine-enriched liquid phase of stage b) is preferably obtained by separating off the biomass from the heated fermentation broth which is enriched with dissolved methionine. To prevent premature crystallization of the methionine, likewise elevated temperature is employed during biomass separation, preferably a temperature in the range specified above.

In a preferred embodiment of the invention d) the crystallized methionine is separated off, e) the solid, preferably crystalline, methionine which has been separated off is if appropriate washed and f) if appropriate dried.

According to a further preferred process variant, the biomass separated off in stage b) is g1) if appropriate washed, the liquid used for the washing being if appropriate heated, and g3) dried.

It can become necessary to heat the wash liquid if, for example, solid methionine is to be present in the biomass fraction separated off, and it is desired to produce methionine from the biomass fraction as far as possible.

To avoid waste streams, preferably g2) the wash liquid produced in stage g1) is combined with the methionine-enriched liquid phase from stage b).

The methionine-containing liquid phases of the stage b) obtained in accordance with the above procedures are then further concentrated, for example by evaporation with heating and if appropriate applying a vacuum. The methionine content in the resultant concentrate is in the range of from about 10 to 40% by weight, based on the total weight of the concentrate. The methionine is preferably separated off by cooling crystallization. For this the solution is cooled to temperatures in the range from 0 to 20° C. After crystallization is complete, the solid methionine is washed with cold wash liquid, for example water, and dried, if appropriate with gentle heating.

According to a further process variant, the mother liquor produced in stage d) is d1) combined with the methionine-containing liquid fraction from another fermentation batch using a methionine-producing microorganism; or d2) added to the biomass separated off from the same or another fermentation batch using a methionine-producing microorganism before the drying according to stage g3).

According to a further process variant, the wash liquid produced in stage e) is e1) combined with the methionine-containing liquid fraction from another fermentation batch using a methionine-producing microorganism; or e2) added to the biomass separated off from the same or another fermentation batch using a methionine-producing microorganism before the drying according to stage g3).

Recirculating mother liquor and wash liquid further prevents production of waste streams.

According to the invention, in addition, preferably, the drying according to stage g3) comprises a spray-drying step.

The present invention further relates to a process for producing methionine by fermentation, a natural or recombinant microorganism being fermented in a manner known per se and the methionine formed being isolated by a process according to the definition above.

In a preferred embodiment, the inventive processes are carried out using a methionine-producing microorganism selected from natural or recombinant bacteria of the genus *Corynebacterium*.

The invention further relates to the use of the dry material obtainable according to the above stage g3) for producing a feedstuff or a feed supplement (feed additive).

The present invention also relates to the use of the inventively isolated methionine for producing a foodstuff or feedstuff or food supplement or feed supplement.

The invention finally relates to methionine-containing dried biomasses obtainable by a process according to the definition above; feed additives, comprising a biomass of this type; and also feed compositions comprising such a feed additive in addition to customary feedstuff constituents.

In the sections below, further developments of the invention are described.

C) Host Cells Used According to the Invention

For the inventive process, use is preferably made of coryneform bacteria. Preferably, these are bacteria of the genus *Corynebacterium*. Of the genus *Corynebacterium*, in particular the species *Corynebacterium glutamicum* is to be mentioned which is known in speciality for its ability to produce L-amino acids.

Examples of suitable strains which may be mentioned are:
of the genus *Corynebacterium*:

*Corynebacterium glutamicum* ATCC 13032, *Corynebacterium acetoglutamicum* ATCC 15806, *Corynebacterium acetoacidophilum* ATCC 13870, *Corynebacterium thermoaminogenes* FERM BP-1539, *Corynebacterium melassecola* ATCC 17965; *Corynebacterium glutamicum* KFCC10065; or *Corynebacterium glutamicum* ATCC21608 or of the genus *Brevibacterium*:

*Brevibacterium flavum* ATCC 14067; *Brevibacterium lactofermentum* ATCC 13869 and *Brevibacterium divaricatum* ATCC 14020 are to be mentioned;

(KFCC=Korean Federation of Culture Collection; ATCC=American Type Culture Collection; FERM BP=Collection of the National Institute of Bioscience and Human-Technology, Agency of Industrial Science and Technology, Japan)

The bacterial strains can be used unmodified or genetically modified in a suitable manner. For instance, microorganisms can be used, for example, in which genes of the methionine biosynthesis pathway are amplified, so that more methionine is present in the cell. Alternatively, or additionally, it is also possible to switch off or attenuate genes which are involved in methionine-degrading metabolic pathways. Suitable strategies for improving methionine production are known from the prior art and are described, for example, in WO-A-02/10209, DE-A-102 170 58, DE-A-102 393 08, DE-A-102 390 73, DE-A-102 390 82 and DE-A-102 228 58 which are expressly incorporated herein by reference.

In order to reduce the activity or amount of an enzyme which could lower the methionine content, those skilled in the art can carry out differing measures individually or in combinations. By reducing the transcription frequency of the gene which codes for the inventive protein, the concentration of the relevant protein can be lowered. This can be achieved by those skilled in the art by modifying or exchanging the promoter or regulation region and also the ribosome binding site of the coding gene. Downstream of the coding region, those skilled in the art can modify terminators or introduce sequences which lead to a reduced stability of the transcript. These measures reducing the life of the mRNA make it possible to lower the expression of the associated protein and thus its concentration.

At the level of the expressed enzyme, fusioned sequences can lead to an increased breakdown rate and thus likewise to a lowering of the concentration of the protein. In addition, those skilled in the art, by means of targeted or untargeted mutagenesis of the coding gene can change the activity, the substrate affinity and the substrate specificity. The activity of enzymes can be affected by mutations in the corresponding genes in such a manner that partial or complete reduction of the reaction velocity of the enzymatic reaction occurs. Examples of such mutations are known to those skilled in the art (Motoyama H. Yano H. Terasaki Y. Anazawa H. Applied & Environmental Microbiology. 67:3064-70, 2001, Eikmanns B J. Eggeling L. Sahm H. Antonie van Leeuwenhoek. 64:145-63, 1993-94). Mutants of the protein can also lead to reduced or inhibited homo- or heteromultimerization of enzyme complexes and thus likewise to an impairment of the enzymatic properties.

Genes modified in this manner can either be present in plasmids, or preferably integrated in the chromosome. In this case, the original gene which has not been modified in this manner can still additionally be present, but preferably can be exchanged for the modified gene.

To reduce the activity of an enzyme measured in a coryneform bacterium, it can be sufficient to express genes which code for functional equivalents, such as artificially manufactured mutants or natural homologes from other organisms. In this case, the original gene can still additionally be present, but preferably can be exchanged for the modified or homologous gene.

In addition, it can be advantageous for the bacterial production of methionine to amplify one or more enzymes of the methionine biosynthesis pathway, of the cysteine metabolic pathway, of aspartate semialdehyde synthesis, of glycolysis, of anaplerosis, of pentose phosphate metabolism, of the citric acid cycle or of amino acid export.

For instance, for the production of methionine, one or more of the following genes can be amplified:

the gene lysC coding for an aspartate kinase (EP 1 108 790 A2; DNA-SEQ NO. 281), the gene asd coding for an aspartate semialdehyde (EP 1 108 790 A2; DNA-SEQ NO. 282), the gene gap coding for glyceraldehyde-3-phosphate dehydrogenase (Eikmanns (1992), Journal of Bacteriology 174: 6076-6086), the gene pgk coding for 3-phosphoglycerate kinase (Eikmanns (1992), Journal of Bacteriology 174: 6076-6086), the gene pyc coding for pyruvate carboxylase (Eikmanns (1992), Journal of Bacteriology 174: 6076-6086), the gene tpi coding for triose-phosphate isomerase (Eikmanns (1992), Journal of Bacteriology 174: 6076-6086), the gene metA coding for homoserine O-acetyltransferase (EP 1 108 790 A2; DNA-SEQ NO. 725), the gene metB coding for cystathioninegamma-synthase (EP 1 108 790 A2; DNA-SEQ NO. 3491), the gene metC coding for cystathioninegamma-lyase (EP 1 108 790 A2; DNA-SEQ NO. 3061), the gene metH coding for cystathioninesynthase (EP 1 108 790 A2; DNA-SEQ NO. 1663), the gene glyA coding for serinehydroxymethyltransferase (EP 1 108 790 A2; DNA-SEQ NO. 1110), the gene metY coding for O-acetylhomoserinesulfhydrylase (EP 1 108 790 A2;DNA-SEQ NO. 726), the gene metF coding for methylenetetrahydrofolatereductase (EP 1 108 790 A2; DNA-SEQ NO. 2379), the gene serC coding for phosphoserine aminotransferase (EP 1 108 790 A2; DNA-SEQ NO. 928)

a gene serB coding for phosphoserine phosphatase (EP 1 108 790 A2; DNA-SEQ NO. 334, DNA-SEQ NO. 467, DNA-SEQ NO. 2767)

the gene cysE coding for serine acetyl-transferase (EP 1 108 790 A2; DNA-SEQ NO. 2818)

the gene cysK coding for cysteine synthase (EP 1 108 790 A2; DNA-SEQ NO. 2817), the gene hom coding for a homoserine dehydrogenase (EP 1 108 790 A2; DNA-SEQ NO. 1306)

In addition, it can be advantageous for the inventive production of methionine to mutate simultaneously at least one of the following genes in such a manner that the activity of the corresponding proteins, compared with non-mutated proteins, is affected to a lesser extent, or is not affected, by a metabolite, or that their specific activity is increased:

the gene lysC coding for an aspartate kinase (EP 1 108 790 A2; DNA-SEQ NO. 281), the gene pyc coding for pyruvate carboxylase (Eikmanns (1992), Journal of Bacteriology 174: 6076-6086), the gene metA coding for homoserine O-acetyltransferase (EP 1 108 790 A2; DNA-SEQ NO. 725), the gene metB coding for cystathionine gamma-synthase (EP 1 108 790 A2; DNA-SEQ NO. 3491), the gene metC coding for cystathionine gamma-lyase (EP 1 108 790 A2; DNA-SEQ NO. 3061), the gene metH coding for methionine synthase (EP 1 108 790 A2; DNA-SEQ NO. 1663), the gene glyA coding for serine hydroxymethyltransferase (EP 1 108 790 A2; DNA-SEQ NO. 1110), the gene metY coding for O-acetylhomoserine sulfhydrylase (EP 1 108 790 A2; DNA-SEQ NO. 726), the gene metF coding for methylenetetrahydrofolate reductase (EP 1 108 790 A2; DNA-SEQ NO. 2379), the gene serC coding for phosphoserine aminotransferase (EP 1 108 790 A2; DNA-SEQ NO. 928)

a gene serB coding for phosphoserine phosphatase (EP 1 108 790 A2; DNA-SEQ NO. 334, DNA-SEQ NO. 467, DNA-SEQ NO. 2767)

the gene cysE coding for serine acetyltransferase (EP 1 108 790 A2; DNA-SEQ NO. 2818)

the gene cysK coding for cysteine synthase (EP 1 108 790 A2; DNA-SEQ NO. 2817), the gene hom coding for a homoserine dehydrogenase (EP 1 108 790 A2; DNA-SEQ NO. 1306)

In addition, it can be advantageous for the production of methionine to attenuate one or more of the following genes, in particular to reduce or switch off their expression:

the gene metK coding for S-adenosylmethionine synthase (E.C.2.5. 1.6)

the gene thrB coding for homoserine kinase (EP 1 108 790 A2; DNA-SEQ NO. 3453)

the gene ilvA coding for threonine dehydratase (EP 1 108 790 A2; DNA-SEQ NO. 2328)

the gene thrC coding for threonine synthase (EP 1 108 790 A2; DNA-SEQ NO. 3486)

the gene ddh coding for meso-diaminopimelate D-dehydrogenase (EP 1 108 790 A2; DNA-SEQ NO. 3494)

the gene pck coding for phosphoenolpyruvate carboxykinase (EP 1 108 790 A2; DNA-SEQ NO. 3157)

the gene pgi coding for glucose-6-phosphate 6-isomerase (EP 1 108 790 A2; DNA-SEQ NO. 950)

the gene poxB coding for pyruvate oxidase (EP 1 108 790 A2; DNA-SEQ NO. 2873)

the gene dapA coding for dihydrodipicolinate synthase (EP 1 108 790 A2; DNA-SEQ NO. 3476)

the gene dapB coding for dihydrodipicolinate reductase (EP 1 108 790 A2; DNA-SEQ NO. 3477)

gene lysA coding for diaminopicolinate decarboxylase (EP 1 108 790 A2; DNA-SEQ NO. 3451)

In addition it can be advantageous for the production of methionine to mutate at least one of the abovementioned genes metK, thrB, ilvA, thrC, ddh, pck, pgi, poxB, dapA, dapB, lysA in such a manner that the enzymatic activity of the corresponding protein is partially or completely cut back.

In addition it can be advantageous for the production of methionine to eliminate further unwanted side reactions (Nakayama: "Breeding of Amino Acid Producing Microorganisms", in: Overproduction of Microbial Products, Krumphanzl, Sikyta, Vanek (eds.), Academic Press, London, UK, 1982).

To achieve overexpression, those skilled in the art can take differing measures individually or in combination. Thus, the number of copies of the corresponding genes can be increased, or the promoter and regulation region or the ribosome binding site which is upstream of the structural gene can be mutated. Expression cassettes act in the same manner which are incorporated upstream of the structural gene. By means of inducible promoters it is additionally possible to increase the expression in the course of production of L-methionine by fermentation. Measures to prolong the life of the mRNA likewise improve expression. Furthermore, by inhibiting the breakdown of the enzyme protein, the enzyme activity is likewise increased. The genes or gene constructs can be present in plasmids with differing numbers of copies or integrated in the chromosome and amplified. Alternatively, overexpression of the relevant genes can further be achieved by changing the media composition and culture conditions.

Those skilled in the art find instructions in this respect, inter alia, in Martin et al. (Biotechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP 0472869, in U.S. Pat. No. 4,601,893, in Schwarzer and Pühler (Biotechnology 9, 84-87 (1991), in Remscheid et al. (Applied and Environmental Microbiology 60, 126-132 (1994), in LaBarre et al. (Journal of Bacteriology 175, 1001-1007 (1993)), in WO 96/15246, in Malumbres et al. (Gene 134, 15-24 (1993)), in JP-A-10-229891, in Jensen and Hammer (Biotechnology and Bioengineering 58, 191-195 (1998)), in Makrides (Microbiological Reviews 60:512-538 (1996) and in known textbooks of genetics and molecular biology.

D) Carrying Out the Inventive Fermentation

The microorganisms produced according to the invention can be cultured for the production of methionine continuously or batchwise in the batch process (batch culture) or in the fed batch process, or repeated fed batch process. A summary of known culture methods may be found in the textbook by Chmiel (Bioprozeβtechnik 1. Einführung in die Bioverfahrenstechnik [Process Biotechnology 1. Introduction to process biotechnology] (Gustav Fischer Verlag, Stuttgart, 1991)) or in the textbook by Storhas (Bioreaktoren und periphere Einrichtungen [Bioreactors and peripherals] (Vieweg Verlag, Brunswick/Wiesbaden, 1994)).

The culture medium to be used has to satisfy the requirements of the respective strains in a suitable manner. Descriptions of culture media of various microorganisms are given in the manual "Manual of Methods für General Bacteriology" of the American Society für Bacteriology (Washington D.C., USA, 1981).

The media which can be used according to the invention usually comprise one or more carbon sources, nitrogen sources, inorganic salts, vitamins and/or trace elements.

Preferred carbon sources are sugars, such as mono-, di- or polysaccharides. Very good carbon sources are, for example, glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of various carbon sources. Other possible carbon sources are oils and fats, for example soybean oil, sunflower oil, peanut oil and coconut fat; fatty acids, for example palmitic acid, stearic acid or linoleic acid; alcohols, for example glycerol, methanol or ethanol; and organic acids, for example acetic acid or lactic acid.

Nitrogen sources are usually organic or inorganic nitrogen compounds or materials which contain these compounds. Examples of nitrogen sources comprise ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soybean meal, soybean protein, yeast extract, meat extract and others. The nitrogen sources can be used individually or as a mixture.

Inorganic salt compounds which can be present in the media comprise the chloride, phosphorus or sulfate salts of calcium, magnesium, sodium, cobalt, molybdenum, potassium, manganese, zinc, copper and iron.

Sulfur sources which can be used for the production of methionine are inorganic sulfur compounds, for example sulfates, sulfites, dithionites, tetrathionates, thiosulfates, sulfides, but also organic sulfur compounds, such as mercaptans and thiols.

As phosphorus source, use can be made of phosphoric acid, potassium dihydrogen phosphate or dipotassium hydrogen phosphate or the corresponding sodium salts.

Chelating agents can be added to the medium to keep metal ions in solution. Particularly suitable chelating agents comprise dihydroxyphenols, such as catechol or protocatechuate, or organic acids, such as citric acid.

The fermentation media used according to the invention usually also comprise other growth factors, such as vitamins or growth promoters, which include, for example, biotin, riboflavin, thiamine, folic acid, nicotinic acid, panthothenate and pyridoxine. Growth factors and salts frequently originate from complex media components, such as yeast extract, molasses, corn steep liquor and the like. In addition, suitable precursors can be added to the culture medium. The exact composition of the media compounds depends greatly on the respective experiment and is decided individually for each specific case. Information on media optimization is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media may also be obtained from commercial suppliers, such as Standard 1 (Merck) or BHI (Brain heart infusion, DIFCO) and the like.

All media components are sterilized either by heat (20 min at 1.5 bar and 121° C.) or by sterile filtration. The components can either be sterilized together or if necessary separately. All media components can be present at the start of the culture or optionally can be added continuously or batchwise.

The temperature of the culture is usually from 15° C. to 45° C., preferably from 25° C. to 40° C., and can be kept constant or changed during the experiment. The pH of the medium should be in the range from 5 to 8.5, preferably around 7.0. The pH for the culture can be regulated during culture by adding basic compounds, such as sodium hydroxide, potassium hydroxide, ammonia or ammonia water, or acidic compounds, such as phosphoric acid or sulfuric acid. To control foam development, antifoamers can be used, for example fatty acid polyglycol esters. To maintain the stability of plasmids, suitable selective substances, for example antibiotics, can be added to the medium. To maintain aerobic conditions, oxygen or oxygen-containing gas mixtures, for example ambient air, are introduced into the culture. The culture is continued until a maximum of the desired product has formed. This goal is usually achieved within from 10 hours to 160 hours.

The resultant methionine-containing fermentation broths usually have a dry mass of from 7.5 to 25% by weight.

It is, furthermore, advantageous if the fermentation is run under sugar-limiting conditions at least at the end, but in particular over at least 30% of the fermentation time. That is to say that during this time the concentration of utilizable sugar in the fermentation medium is kept at from $\geq 0$ to 3 g/l, or is reduced.

E) Purification of Methionine

If the methionine obtained according to the invention after crystallization should still not have the desired purity, it can be further purified. For this the product is subjected in dissolved form to chromatography using a suitable resin, the desired product or the impurities being wholly or partially retained on the chromatographic resin. These chromatographic steps can be repeated if necessary, the same or different chromatographic resins being used. Those skilled in the art are conversant in the selection of suitable chromatographic resins and their most effective application. The purified product can be concentrated by filtration or ultrafiltration and stored at a temperature at which the stability of the product is maximal.

The identity and purity of the isolated compound can be determined by known techniques. These include high-performance liquid chromatography (HPLC), spectroscopic methods, color methods, thin-layer chromatography, NIRS, enzyme testing or microbiological tests. These analytical methods are summarized in: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

F) Drying the Biomass

After the fermentation is completed, the methionine-containing fermentation broth can be processed directly to give the finished dry feedstuff additive. According to a preferred embodiment of the invention, however, first the biomass content is wholly or partially, preferably completely, removed, for example by centrifugation, from the fermentation broth and processed to form inventive feedstuff additive. The resultant biomass still contains a certain fraction of methionine, which if desired can be decreased by intermediate provision of a wash step.

The inventive biomass can be worked up to give a suitable dry product by various processes from the prior art which are known per se. In particular, suitable processes for the production are drying processes, such as spray drying, spray granulation, contact drying, fluidized-bed drying or freeze drying. Suitable processes are described, for example in:

O. Krischer, W. Kast, *Trocknungstechnik* [Drying technology] first volume, "Die wissenschaftlichen Grundlagen der Trocknungstechnik" [The scientific bases of drying technology], Springer-Verlag 1978; Krischer/Kröll, *Trocknungstechnik* [Drying technology] second volume, "Trockner und Trocknungsverfahren" [Dryers and drying methods], Springer-Verlag 1959; K. Kröll, W. Kast, *Trocknungstechnik* third volume, "Trocknen und Trockner in der Produktion" [Drying and dryers in production], Springer-Verlag 1989; K. Masters, "Spray Drying Handbook", Longman Scientific & Technical 1991, 725 pages; H. Uhlemann, L. Mörl, "Wirbelschicht—Sprühgranulation" [Fluidized-bed spray granulation], Springer-Verlag 2000; Freeze drying: Georg-Wilhelm Oetjen, "Gefriertrocknen" [Freeze drying], VCH 1997; and also EP-A-0 809 940. The disclosure of the above-described publications is expressly incorporated herein by reference.

Particularly preferably, the inventive drying step is performed by spray drying, for example spray drying with an integrated fluidized bed, or by spray granulation.

If desired, the drying can be performed in the presence of a suitable support material which is suitable for feedstuff use, as a result of which, in particular, the free-flowing ability and thus the product quality can be improved.

Support materials which are suitable for feedstuff use and which can be used are customary inert supports. An "inert" support shall not exhibit any adverse interactions with the food adjuncts present in the additive and must be safe for use as aid in feedstuff additives. Examples of suitable support materials which may be mentioned are: inorganic or organic compounds of natural or synthetic origin. Examples of suitable low-molecular-weight inorganic supports are salts, such as sodium chloride, calcium carbonate, sodium sulfate and magnesium sulfate, or silicic acid. Examples of suitable organic supports are, in particular, sugars, for example glucose, fructose, sucrose and also dextrins and starch products. Examples of higher-molecular-weight organic supports which may be mentioned are: starch and cellulose preparations, such as, in particular, corn starch, cereal flours, for example wheat, rye, barley and oat flour, or mixtures thereof, or wheat semolina bran. The support material can be present in the preparation, based on dry basis, in a quantity of from about 5 to 85% by weight, for example from about 10 to 30% by weight, from 20 to 40% by weight or from 50 to 85% by weight.

Hereinafter, some preferred drying techniques are to be dealt with briefly in general form.

The spray drying can be carried out by first pumping the still-moist biomass to the atomizer in the spray tower. The atomization is performed, for example, by means of a pressure nozzle (single-component nozzle), a two-component nozzle or a centrifugal atomizer. The droplets are dried by a hot air stream passed into the spray dryer. When centrifugal atomizers are used, the drying is preferably performed in cocurrent flow. When nozzles are used, the drying can also be performed in countercurrent flow or crossflow. The dried powder can be discharged at the tower or it is carried along with the air stream and separated in a cyclone and/or filter. Depending on the product and procedure, a post-drying may be required, which can be performed in an internal fluidized bed flanged to the spray dryer or in an external fluidized bed.

In a variant of the inventive drying process, a continuous or batchwise fluidized-bed agglomeration is provided downstream of the drying step, in particular the spray drying. For this, a fluidized-bed dryer is charged, at the start of the process, with a pulverulent material, for example pulverulent additive obtained by spray drying. The material is fluidized, for example, by feeding preheated air. A liquid phase, for example further biomass or a binder-containing solution, is sprayed onto the fluidized bed, and as a result the powder which has been charged is wetted with this solution and, by its adhesive properties, increasingly agglomerated. At the same time, continuously or semicontinuously, in cycles at intervals, a subquantity of agglomerate is discharged from the fluidized bed. The discharge is classified, for example using a screen. Coarse material produced in this procedure can be ground and continuously recirculated to the fluidized bed. Fines, for example from the exhaust air filter system, can likewise be continuously recirculated.

A further preferred process variant comprises spray drying biomass to give a powder, coupled with the subsequent agglomeration of the spray-dried powder. This can be performed batchwise or continuously. Preference is given to the continuous procedure. Processes of this type can be carried out using conventional spray-drying plants. Advantageously, however, the procedure is carried out in apparatuses which are known as FSD (fluidized spray dryer), SBD (spray bed dryer) or MSD (multi stage dryer).

A fluidized spray dryer (FSD) drying plant for continuous production of an inventive dry product can be operated in particular according to the following pathline: wet biomass is introduced via a feedline into the top of the FSD dryer and atomized using an atomizer. The drying is performed by introducing air in cocurrent flow. The air is preheated via a heater. The spray-dried powder collects in the integrated fluidized bed in the bottom of the FSD dryer and is there sprayed using a spraying apparatus using compressed air, for example, with a binder solution and fluidized using introduced air. The air for this is preheated and fed via a feedline beneath the gas distributor of the integrated fluidized bed. The resultant preagglomerate then passes into a downstream external fluidized bed. Preheated air is introduced into this external fluidized bed from beneath via a further feedline. The preagglomerate charged in the fluidized bed is again sprayed using a further spraying apparatus using compressed air (for example with binder solution) and agglomerated to form the end product. The finished agglomerate is discharged from the fluidized bed and can be further worked up as described above.

The composition and amount of the liquids sprayed depend on the adhesive properties of the solution sprayed in, the agglomerate size to be achieved and the process conditions.

In the event that the adhesive properties of the sprayed biomass are not sufficient to ensure that the particles stick together stably after spraying, the use of a binder in addition is advantageous. This avoids that the agglomerates disintegrate again on drying. In such cases it is preferred to spray a binder which is soluble or dispersible in an aqueous medium into the fluidized bed. Examples of suitable binders which may be mentioned are solutions of carbohydrates, for example glucose, sucrose, dextrins etc., sugar alcohols, for example mannitol, or polymer solutions, for example solutions of hydroxypropylmethylcellulose (HPMC), polyvinylpyrrolidone (PVP), ethoxylated cellulose (EC), ethylcellulose or propylcellulose. As a result of suitable choice of amount and adhesive properties of the binder sprayed in, agglomerates of differing size and strength are formed.

If the binder is sprayed on as a separate solution, the binder content of the solution is in the range of from about 1 to 30% by weight, based on the total weight of the solution. The binder is likewise present in this case dissolved in an aqueous medium, preferably sterile demineralized water. Customary additives, for example buffer or solubilizer, can likewise be present.

The content of binder in the end product is according to the invention from 0 to about 20% by weight, for example from about 1 to 6% by weight. The optimum amount is also a function of the type of binder selected. It is necessary to ensure that adverse effects on the product are avoided.

G) Formulations i) Feedstuff Additives and Feedstuff Compositions:

The inventive methionine-containing feedstuff additive is preferably in the form of a finely divided free-flowing powder, or in granulated form. Particles can be, for example in a size range of from 5 to 200 μm, for example from 10 to 150 μm, from 20 to 100 μm or from 30 to 80 μm, without being restricted thereto.

The bulk density of the inventive additives can be, for example, in the range of from about 100 to 600 g/l, for example from 150 to 400 g/l, or from 200 to 350 g/l, without being restricted thereto.

The methionine content of the inventive additive varies according to the manner of production.

Methionine crystals available according to the invention have a methionine content of greater than 60% by weight, for example of from about 70 to 98% by weight, preferably from about 80 to 95% by weight, particularly preferably from about 87 to 95% by weight. The content of salts (residues from the fermentation broth) can be in the range of from about 0 to 20% by weight, in particular of from about 5 to 15% by weight. Other fermentation minor constituents can be present in an amount of from about 0 to 20% by weight, in particular of from about 5 to 15% by weight.

Biomass methionine of the invention has a methionine content of more than 3% by weight, for example from about 5 to 40% by weight, or from about 10 to 35% by weight. The content of salts can be in the range of from about 0 to 30% by weight, such as from about 5 to 25% by weight. Other minor fermentation constituents can be present at a content of from about 0 to 20% by weight, such as from about 5 to 15% by weight.

The residual moisture content of the finished additive is preferably in the range of less than about 3-5% by weight, based on the total weight of the additive. The above percentages by weight are based on the total weight of the dry product (preferably without residual moisture).

In addition to the above-described constituents, the inventive formulations, as already mentioned above, can comprise further adjuncts, which can be added before, during or after workup of the biomass. Examples which can be mentioned are preservatives, antibiotics, antimicrobial additives, antioxidants, chelating agents, physiologically harmless salts, flavorings, colorings and the like. Nutritionally relevant adjuncts can also be present, for example vitamins (for example vitamins A, $B_1$, $B_2$, $B_6$, $B_{12}$, C, $D_3$, and/or E, $K_3$, folic acid, nicotinic acid, pantothenic acid); taurine, carboxylic acids and salts thereof, for example tricarboxylic acids, such as citrate, isocitrate, trans-/cisaconitate and/or homocitrate, enzymes, carotenoids, minerals, for example P, Ca, Mg and/or Fe, and trace elements, such as Se, Cr, Zn, Mn, proteins, carbohydrates, fats, amino acids. In addition pyruvic acid, L-carnitine, lipoic acid, coenzyme Q10, aminocarboxylic acids, for example creatine, orotic acid, myoinositol, flavonoids, betaine, p-aminobenzoic acid can be present.

The inventive methionine-containing feed additives can be incorporated into commercially conventional animal feed formulations, which can then be fed, for example, to cattle, pigs, sheep, poultry and the like. For this the inventive additive is mixed with customary animal feed constituents and if appropriate processed into final form, for example pelleted. Customary animal feed constituents are, for example, corn, barley, manioc, oats, soybean, fishmeal, wheat semolina bran, soybean oil, chalk, minerals, trace elements, amino acids and vitamins.

ii) Food and Feed Supplements

The inventively produced methionine is used as an adjunct in foodstuffs and feedstuffs or as an adjunct in food supplements and feed supplements, for example multivitamin preparations. The inventively produced product can be incorporated for this in the desired amount and in a manner known per se into conventional foodstuffs and feedstuffs or food supplements and feed supplements. The methionine can be present in this case, depending on use, in differing expedient amounts.

iii) Coated Formulations

The above-described inventive formulations can if appropriate additionally have a coating. They are furnished in this case with a coating composition which comprises at least one compound selected from:

poly(alkylene glycol)s, in particular poly(ethylene glycol)s, for example having a number-average molecular weight of from about 400 to 15 000, for example from 400 to 10 000;

poly(alkylene oxide) polymers or copolymers, for example having a number-average molecular weight of from about 4000 to 20 000, in particular block copolymers of polyoxyethylene and polyoxypropylene;

substituted polystyrenes, maleic acid derivatives and styrene-maleic acid copolymers;

vinyl polymers, in particular polyvinylpyrrolidones, for example having a number-average molecular weight of from about 7000 to 1 000 000; either alone or in combination with other compounds, such as cellulose ethers or starches;

vinylpyrrolidone/vinyl acetate copolymers, for example having a number-average molecular weight of from about 30 000 to 100 000;

poly(vinyl alcohol)s, for example having a number-average molecular weight of from about 10 000 to 200 000, and poly(phthalic acid vinyl ester)s;

hydroxypropylmethylcelluloses, for example having a number-average molecular weight of from about 6000 to 80 000;

alkyl(meth)acrylate polymers and copolymers, for example having a number-average molecular weight of from about 100 000 to 1 000 000, in particular ethyl acrylate/methyl methacrylate copolymers and methacrylate/ethyl acrylate copolymers;

poly(vinyl acetate)s, for example having a number-average molecular weight of from about 250 000 to 700 000, if appropriate stabilized with poly-vinylpyrrolidone;

polyalkylenes, in particular polyethylenes;

aromatic polymers, for example lignins;

poly(acrylic acid)s;

polyacrylamides;

polycyanoacrylates;

phenoxyacetic acid-formaldehyde resins;

cellulose derivatives, such as ethylcellulose, ethylmethylcellulose, methylcellulose, hydroxypropylcellulose, hydroxypropylmethylcellulose, carboxymethylcellulose, cellulose acetate phthalate;

animal, vegetable or synthetic fats and modified fats, for example polyglycols, fatty alcohols, ethoxylated fatty alcohols, higher fatty acids; mono-, di- and triglycerides of higher fatty acids, for example glyceryl monostearate, alkylarylethoxylates and cocomonoethanolamides;

animal and plant waxes or chemically modified animal and plant waxes, such as beeswax, candelilla wax, carnauba wax, montan ester wax and rice germ oil wax, spermaceti, lanolin, jojoba wax, sasol wax;

animal and vegetable proteins, for example gelatin, gelatin derivatives, gelatin substitutes, casein, whey, keratin, soybean protein; zein and wheat protein;

mono- and disaccharides, oligosaccharides, polysaccharides, for example hyaluronic acid, pullulan, elsinan, starches, modified starches, and also pectins, alginates, chitosan, carrageenan;

vegetable oils, for example sunflower, thistle, cottonseed, soybean, corn germ, olive, rapeseed, linseed, coconut, palm kernel oils; synthetic or semisynthetic oils, for example medium-chain triglycerides or mineral oils; animal oils, for example herring, sardine and whale oils;

hardened (hydrogenated or partially hydrogenated) oils/fats, for example of the abovementioned, in particular hydrogenated palm oil, hydrogenated cottonseed oil, hydrogenated soybean oil;

lacquer coatings, for example terpenes, in particular shellack, tolubalsam, perubalsam, sandarac, and silicone resins;

fatty acids, both saturated and also monounsaturated and polyunsaturated $C_6$ to $C_{24}$-carboxylic acids;

silicas;

and mixtures thereof.

Adding plasticizers or emulsifiers to fats or waxes before coating can if appropriate be advantageous to improve the flexibility of the film.

Coatings are applied in a manner known per se, if appropriate together with additives, generally via devices for making addition dropwise or by spraying onto the product of value which has been charged in a mixer. Examples of this are lances, sprinkler heads, single-fluid or multiple-fluid nozzles, or rotating dropping or atomizing devices. In the simplest case it is possible also to make the addition locally as a concentrated jet. Alternatively, the coating material can first be charged into the mixer, in order thereafter to add the product of value. Another possibility is the addition of initially solid coating material which, as a result of wall heating, or owing to mechanical energy input, melts and coats the product of value.

The invention will now be described in more detail with reference to the accompanying figures. FIGS. 1 to 4 show different developments of an inventive process for producing crystalline dry methionine and dry methionine-containing biomass ("biomass methionine").

EXAMPLE 1 a) Production of Methionine by Fermentation

To produce a representative fermentation broth for the purification of methionine, a laboratory fermentation was carried out. The *Corynebacterium glutamicum* strain ATCC13032 (American Type Culture Collection, Manassas, USA) was grown in a preliminary culture of 200 ml of BHI medium (Difco/Becton Dickinson Franklin Lakes, USA). In the Techfors fermenter, the preliminary culture was then inoculated into the culture medium (approximately 14 l).

The fermentation medium of the main culture had the following composition 2 g/l of $KH_2PO_4$
2 g/l of $K_2HPO_4$
10 g/l of ammonium sulfate
100 g/l of glucose
5 g/l of yeast extract
20 mg/l of kanamycin
1 g/l of KS911 ASM antifoam
pH 7.0 made up with demineralized water to the desired final volume

Trace salt solution 1 ml/l of medium

| | |
|---|---|
| $FeSO_4 \cdot 7 H_2O$ | 10 g/l |
| $MnSO_4 \cdot 4-6 H_2O$ | 10 g/l |
| $ZnSO_4$ | 2 g/l |
| $MgSO_4 \cdot 7 H_2O$ | 250 g/l |
| Adjust to pH 1 using HCl | |

1 ml/l of protocatechuate solution (stock solution 300 mg/10 ml)

| | |
|---|---|
| biotin | 1 mg/l |
| thiamine | 1 mg/l |
| $CaCl_2$ | 5 mg/l |

After the fermenter has been inoculated by the preliminary culture, the fermenter was kept at pH 7 by adding base (25% $NH_4OH$) and fermented until the sugar had been consumed. This was indicated by an increase in the $pO_2$ value or by a decrease in OTR and CTR.

b) Workup of the Fermentation Broth

Figure 1:
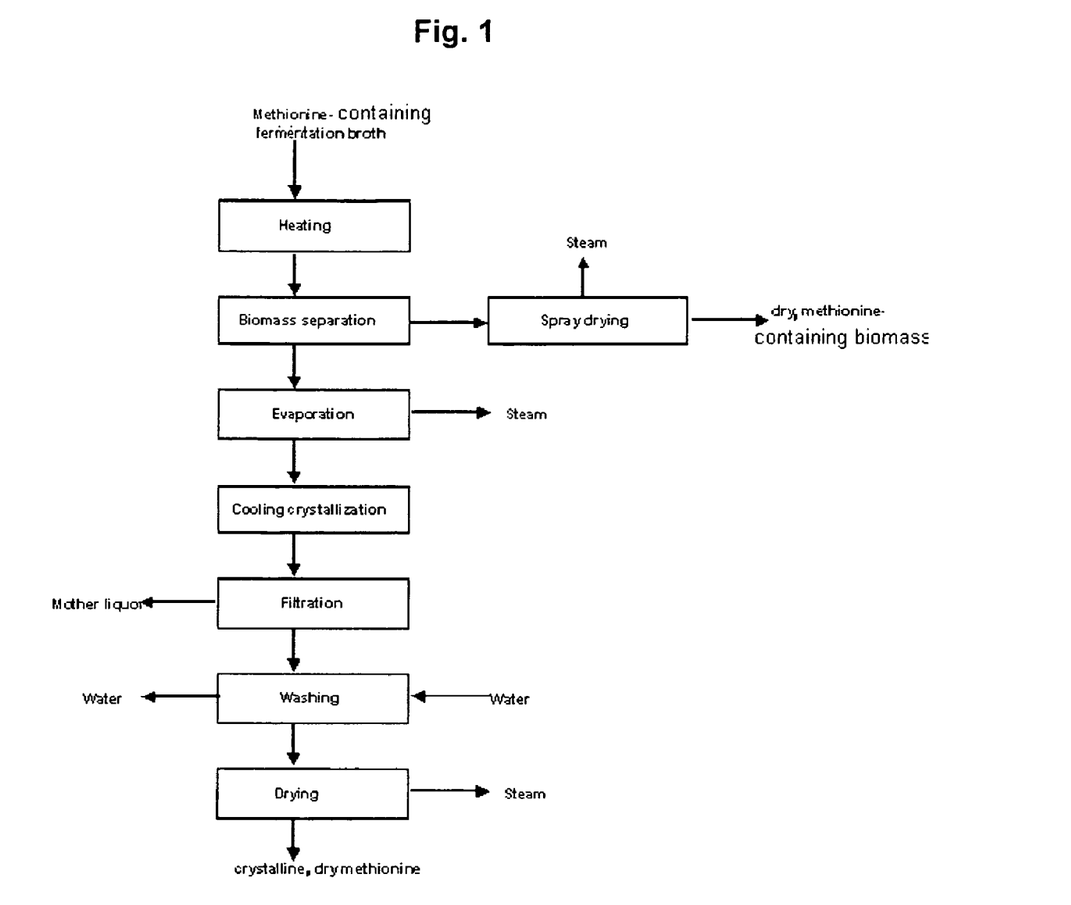

The procedure for the workup is outlined diagrammatically in FIG. 1.

The fermentation broth produced according to section a) acts as starting material. At a fermentation temperature between 30 and 40° C., approximately 50% of the methionine present is in crystalline form. The starting product has a water content of approximately 86%, a fortified methionine content of approximately 9% and a biomass content of approximately 3%. Other fermentation by-products and minerals are present in the fermentation broth in traces (approximately 2.5% by weight).

20 kg of this fermentation broth are heated at 70° C. for 15 minutes. The methionine passes completely into solution as a result. At a constant temperature, the biomass is then centrifuged off. The supernatant (approximately 15 kg) is then concentrated to a methionine content of 20% at 100° C. and atmospheric pressure. The concentrate is then cooled to 5° C. at 5 K/h, as a result of which a majority of the methionine crystallizes out. The crystals are then separated off from the crystal magma on a vacuum filter, washed with 4 liters of water previously equilibrated at 5° C. and then blown dry with nitrogen at 40° C. By means of this procedure, 1.3 kg of dry methionine were isolated at a purity of approximately 90%.

The residue of the centrifugation (approximately 5 kg), in addition to dry biomass, also comprises approximately 6% methionine. By spray drying, this residue can be converted into approximately 0.7 kg of slightly yellowish and free-flowing dry powder having a residual moisture of 3%, which, in addition to the dry biomass and other fermentation by-products and mineral salts, also comprises methionine (approximately 30%).

The spray drying was performed in a laboratory spray dryer using the following instrument settings:

Inlet temperature: 200° C.,

Outlet temperature: 80-82° C.

The heating gas used was 60 m³/h of nitrogen. The nozzle gas was sprayed at a pressure of 2 bar through a 1.2 mm nozzle.

EXAMPLE 2

Figure 2:
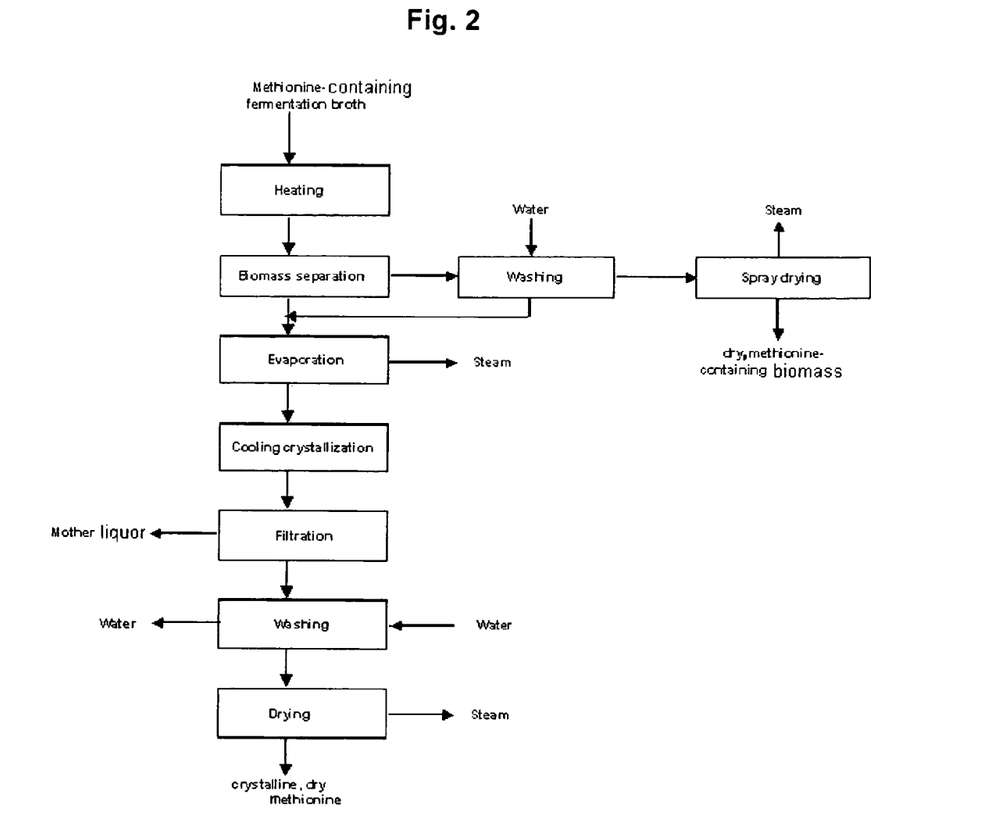

Starting from the same starting material, the process is modified to the extent that the biomass is separated off by means of centrifugation and the biomass which is separated off is then washed with 5 l of water (FIG. 2). After centrifugation, the resulting supernatant is added to the supernatant of the first biomass separation. The entire supernatant is concentrated to a methionine content of 16% at 100° C. and atmospheric pressure. By cooling the concentrate to 5° C. at 5 K/h, the methionine is crystallized out. The crystals are separated off on a vacuum filter, washed with 4.5 liters of water previously equilibrated at 5° C. and then dried with nitrogen at 40° C. By means of this procedure, the amount of dry methionine is increased to approximately 1.5 kg. The purity of the isolated crystals is again approximately 90%.

The residue of the biomass which is separated off and washed is converted into approximately 0.5 kg of dry product by spray drying.

The product thus produced which, in addition to dry biomass and other fermentation by-products and mineral salts, also comprises methionine (approximately 10%), was free flowing.

EXAMPLE 3

Figure 3:
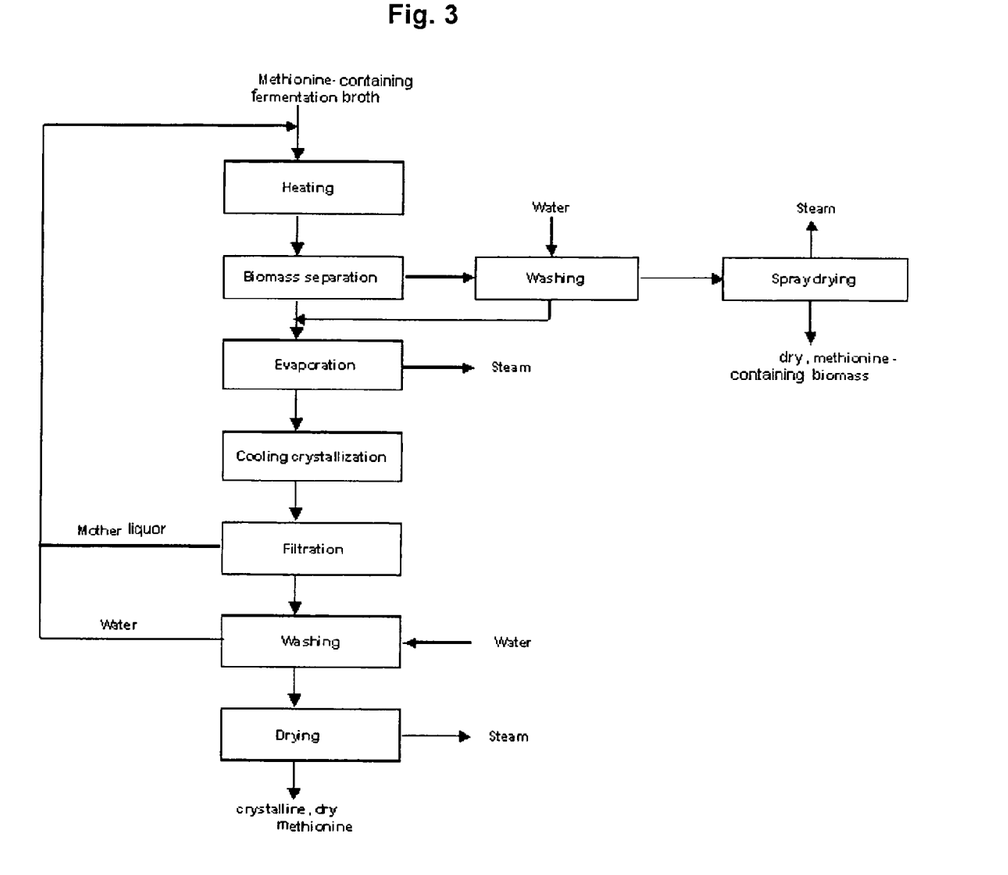

Starting from the same starting material, the process of Example 2 was additionally modified to the extent that the mother liquor and the wash water which are produced when the crystalline methionine is separated off are added in a next batch to the methionine-containing fermentation broth (FIG. 3).

With an otherwise similar procedure to Example 2, in the fermentation approximately 1.5 kg of dry methionine are obtained from the crystallization at a purity of approximately 90% and approximately 0.5 kg of product is obtained from the spray-dried biomass having a methionine content of approximately 10%.

EXAMPLE 4

Figure 4:
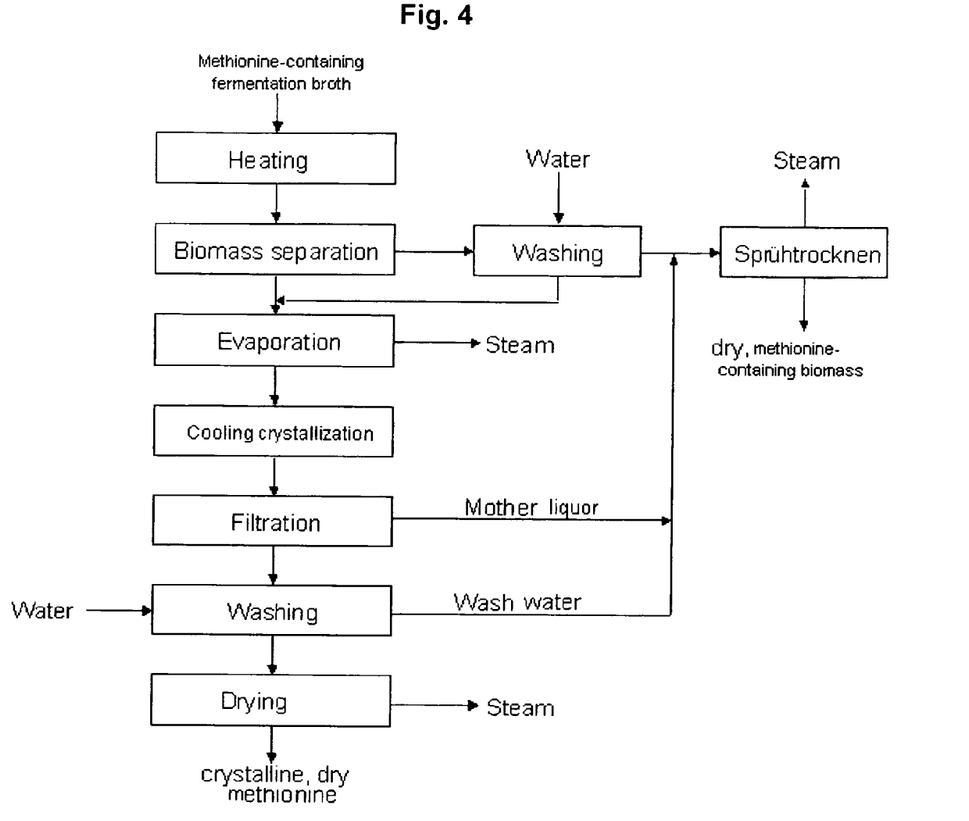

Starting from the same starting material, the process of Example 2 is additionally modified to the extent that the mother liquor and the wash water which are produced when the crystalline methionine is separated off are added to the biomass stream before the spray drying (FIG. 4).

With an otherwise similar procedure to Example 2, approximately 1.1 kg of methionine-containing biomass are produced, which, in addition to dry biomass and other fermentation by-products and mineral salts, also comprises methionine (approximately 30%). The amount of dry methionine is 1.5 kg with a purity of approximately 90%.

EXAMPLE 5

A process variant is also conceivable in which a portion of the mother liquor and of the wash water, after the crystallization of the methionine, is added to the fermenter broth before biomass separation, and the other substream is added to the biomass stream before spray drying (combination of Examples 3 and 4).

We claim:
1. A process for preparing methionine comprising,
   a) culturing a methionine-producing microorganism under conditions appropriate to produce methionine;
   b) heating the culture at 60° C. to 120° C. for a period of time sufficient for solubilizing any methionine which has crystallized; and
   c) while maintaining the temperature at 60° C. to 120° C. separating the fermentation broth from the microorganisms.
2. The process of claim 1, wherein the heating is performed to a temperature of about 70 to 100° C. in stage b).
3. The process of claim 1, further comprising
   d) crystallizing methionine out of the fermentation broth.
4. The process of claim 1, further comprising washing the microorganism to give a spent wash liquid and adding the spent wash liquid to the fermentation broth of step c).
5. The process of 3, further comprising
   e) separating off the crystallized methionine to give a mother liquid,
   f) washing the crystallized methionine which has been separated off to give a wash liquid, and
   g) drying the crystallized methionine.
6. The process of claim 5, wherein the mother liquid produced in stage e) is combined with a methionine-containing liquid fraction from another fermentation batch.
7. The process of claim 5, wherein the wash liquid produced in stage f) is combined with a methionine-containing liquid fraction from another fermentation batch.
8. The process of claim 1, wherein the microorganism is a natural or recombinant microorganism.
9. The process of claim 8, wherein the microorganism is a natural or recombinant bacterium of the genus Corynebacterium.
10. The process of claim 8, wherein L-methionine is produced.
11. The process of claim 1, further comprising concentrating the fermentation broth and then crystallizing methionine out of the concentrated fermentation, broth.
12. The process of claim 4, further comprising drying the washed microorganism.
13. The process of claim 12, wherein the drying comprises spray-drying.
14. The process of claim 1, wherein the amount of methionine in the fraction containing the microorganism ranges from more than 3% to about 40% by weight.
15. The process of claim 5, further comprising separating off the microorganism from the same or another fermentation batch and adding the mother liquid produced in stage e) to the separated off microorganism.
16. The process of claim 5, further comprising separating off the microorganism from the same or another fermentation batch and adding the wash liquid produced in stage f) to the separated off microorganism.

* * * * *